United States Patent
Cho et al.

(10) Patent No.: US 11,439,838 B2
(45) Date of Patent: Sep. 13, 2022

(54) NEURAL PROBE STRUCTURE FOR MEASURING MULTIPLE FLUORESCENCE SIGNALS AND MANUFACTURING METHOD THEREOF

(71) Applicant: KOREA INSTITUTE OF SCIENCE AND TECHNOLOGY, Seoul (KR)

(72) Inventors: Il-Joo Cho, Seoul (KR); Namsun Chou, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/894,887

(22) Filed: Jun. 8, 2020

(65) Prior Publication Data
US 2021/0085996 A1  Mar. 25, 2021

(30) Foreign Application Priority Data

Sep. 19, 2019 (KR) .................. 10-2019-0115488

(51) Int. Cl.
*A61N 5/06* (2006.01)

(52) U.S. Cl.
CPC ......... *A61N 5/0622* (2013.01); *A61N 5/0601* (2013.01); *A61N 2005/063* (2013.01); *A61N 2005/0612* (2013.01); *A61N 2005/0651* (2013.01); *A61N 2005/0667* (2013.01)

(58) Field of Classification Search
CPC ......... A61N 5/0622; A61N 2005/0612; A61N 2005/0667; A61N 2005/063; A61N 5/0601; A61B 5/4064
See application file for complete search history.

(56) References Cited

U.S. PATENT DOCUMENTS

| | | | |
|---|---|---|---|
| 6,760,112 B2 | 7/2004 | Reed et al. | |
| 9,907,496 B1 | 3/2018 | Okandan et al. | |
| 10,182,702 B2 | 1/2019 | Nagao et al. | |
| 2011/0079708 A1* | 4/2011 | Hsin ................ | H03F 3/08 250/214 A |
| 2012/0062723 A1 | 3/2012 | Ghosh et al. | |
| 2014/0256057 A1 | 9/2014 | Ozawa et al. | |

(Continued)

FOREIGN PATENT DOCUMENTS

| | | |
|---|---|---|
| EP | 2736406 A1 | 6/2014 |
| JP | 4581498 B2 | 11/2010 |

(Continued)

OTHER PUBLICATIONS

Luyao Lu et al., "Wireless optoelectronic photometers for monitoring neuronal dynamics in the deep brain," PNAS, Jan. 29, 2018, pp. E1374-E1383, vol. 115, No. 7.

(Continued)

*Primary Examiner* — Carl H Layno
*Assistant Examiner* — Aya Ziad Bakkar
(74) *Attorney, Agent, or Firm* — Cantor Colburn LLP (57) ABSTRACT

A neural probe structure includes a probe that is inserted into a subject, a body to support a rear end of the probe, at least one light source included in the body, a photo diode formed in the probe, and an optical waveguide extending from the at least one light source in the body to the photo diode of the probe, wherein the photo diode is formed at a smaller height than the optical waveguide.

11 Claims, 9 Drawing Sheets

(56) References Cited

U.S. PATENT DOCUMENTS

| | | | |
|---|---|---|---|
| 2016/0150963 A1* | 6/2016 | Roukes | A61B 5/0084 |
| | | | 600/476 |
| 2016/0367836 A1* | 12/2016 | Kampasi | A61N 5/0622 |
| 2019/0091484 A1* | 3/2019 | Lai | A61N 5/0601 |

FOREIGN PATENT DOCUMENTS

| | | |
|---|---|---|
| JP | 6569856 B2 | 9/2019 |
| KR | 1020140068188 A | 6/2014 |
| WO | 2013/016391 A1 | 1/2013 |

OTHER PUBLICATIONS

Fan Wu et al., "An implantable neural probe with monolithically integrated dielectric waveguide and recording electrodes for optogenetics applications," Journal of Neural Engineering, Aug. 28, 2013, 9 pages, vol. 10, No. 056012.

The extended European Search Report for EP Application No. 20178406.3 dated Sep. 15, 2020.

\* cited by examiner

NEURAL PROBE STRUCTURE FOR MEASURING MULTIPLE FLUORESCENCE SIGNALS AND MANUFACTURING METHOD THEREOF

CROSS-REFERENCE TO RELATED APPLICATION

This application claims priority to Korean Patent Application No. 10-2019-0115488, filed on Sep. 19, 2019, and all the benefits accruing therefrom under 35 U.S.C. § 119, the contents of which in its entirety are herein incorporated by reference.

BACKGROUND

1. Field

The present disclosure relates to a neural probe structure for measuring multiple fluorescence signals and a manufacturing method thereof, and more particularly, to a neural probe structure for applying multiple optical neural stimulation using an optical waveguide and collecting multiple fluorescence response signals and a manufacturing method thereof.

Description of Government-Funded Research and Development

This research is conducted by Korean Institute of Science and Technology and funded by the brain science original technology development program, development of MEMS neural probe systems for precise brain signal measurement and brain circuit control (2017M3C7A1028857) in National Research Foundation of Korea, Ministry of Science and ICT, Republic of Korea (percentage contribution 1/3).

This research is also conducted by Korean Institute of Science and Technology and funded by Bio & Medical technology development (R&D), development of multifunctional microsystems for large-scale culture and analysis of organoids (No. 1711081600) in National Research Foundation of Korea, Ministry of Science and ICT, Republic of Korea (percentage contribution 1/3).

This research is also conducted by Korean Institute of Science and Technology and funded by hyperfusion AI original technology development, development of smart plates for precise 3D measurement of neural activity in brain tissues (No. 1711094510) in National Research Foundation of Korea, Ministry of Science and ICT, Republic of Korea (percentage contribution 1/3).

2. Description of the Related Art

Recently, many studies have been made to define neural activity by stimulating a subject's neurons in the brain and sensing and analyzing signals in response to the stimulation. An implantable neural probe is briefly used to directly stimulate the subject's neurons and collect information.

Some of neural probes apply electrical neural stimulation using electrodes integrated in probe bodies. However, electrical neural stimulation may result in nerve damage and is impossible to achieve localized stimulation at a desired part since substances found in the nerves are electrically conductive.

Accordingly, more recently, methods that apply optical neural stimulation using light and collect response signals have been introduced.

An optical stimulation probe has an optical fiber directly attached to a silicon probe body, and is inserted into a subject. In this case, it is difficult to accurately control a stimulation site, and there is an increase in the size of the probe.

Such an optical fiber and lens based optical signal measuring system is required to remove all surrounding tissues to insert the probe into a desired location of the subject due to the size of the probe, which makes it difficult to set up an environment for measuring the subject's neural signals.

Additionally, the size of the probe makes it difficult to simultaneously measure neural signals at many areas, and limits the use in a wide range of neural circuit research applications.

RELATED LITERATURES

Patent Literatures (Patent Literature 1) U.S. Pat. No. 6,760,112 B2

SUMMARY

The present disclosure is designed to solve the above-described problem of the related art, and therefore the present disclosure is directed to providing a neural probe structure that provides a probe of a small size suitable for a usage environment and can measure multiple fluorescence to simultaneously observe many types, and a manufacturing method thereof.

To achieve the above-described object, according to an aspect of the present disclosure, there is provided a neural probe structure including a probe that is inserted into a subject, a body to support a rear end of the probe, at least one light source included in the body, a photo diode formed in the probe, and an optical waveguide extending from the at least one light source in the body to the photo diode of the probe, wherein the photo diode is formed at a smaller height than the optical waveguide.

According to an embodiment of the present disclosure, the neural probe structure may further include an optical filter on the photo diode.

According to an embodiment of the present disclosure, when the body includes a plurality of light sources, the optical waveguide may be formed such that a plurality of branches each extends from the plurality of light sources, the branches are combined into one strand at a point, and the strand extends to the photo diode.

According to an embodiment of the present disclosure, the photo diode may be formed in a concave shape inwards from a surface of the probe to prevent the photo diode from protruding above the surface of the probe.

According to an embodiment of the present disclosure, the neural probe structure may further include a plurality of electrodes formed in the probe.

According to an embodiment of the present disclosure, the photo diode may measure a fluorescence signal emitted from a neuron by light transmitted from the at least one light source through the optical waveguide, and the plurality of electrodes may be arranged near the photo diode to measure an electrical neural signal of the neuron.

According to another aspect of the present disclosure, there is a provided a method for manufacturing the neural probe structure including forming the photo diode in a substrate that constitutes the probe, and forming the optical waveguide at a larger height than the photo diode along a longitudinal axis from the photo diode.

According to an embodiment of the present disclosure, the method for manufacturing a neural probe structure may further include forming an optical filter on the photo diode.

According to an embodiment of the present disclosure, forming the optical waveguide may include, when the body includes a plurality of light sources, forming the optical waveguide such that a plurality of branches each extends from the plurality of light sources, the branches are combined into one strand at a point, and the strand extends to the photo diode.

According to an embodiment of the present disclosure, forming the photo diode in the substrate may include forming the photo diode in a silicon substrate based on a complementary metal-oxide semiconductor (CMOS) process.

According to an embodiment of the present disclosure, forming the photo diode in the substrate may include forming the photo diode in the substrate into a concave shape inwards from a surface of the probe to prevent the photo diode from protruding above the surface of the probe.

According to an embodiment of the present disclosure, the method for manufacturing a neural probe structure may further include forming a plurality of electrodes at locations away a predetermined distance on two sides along a latitudinal axis from the photo diode.

DETAILED DESCRIPTION

Hereinafter, exemplary embodiments of the present disclosure will be described with reference to the accompanying drawings. While the present disclosure is described with reference to the embodiments shown in the drawings, this is described as one embodiment, and the technical spirit of the present disclosure and its essential elements and operations are not limited thereby.

Figure 1:
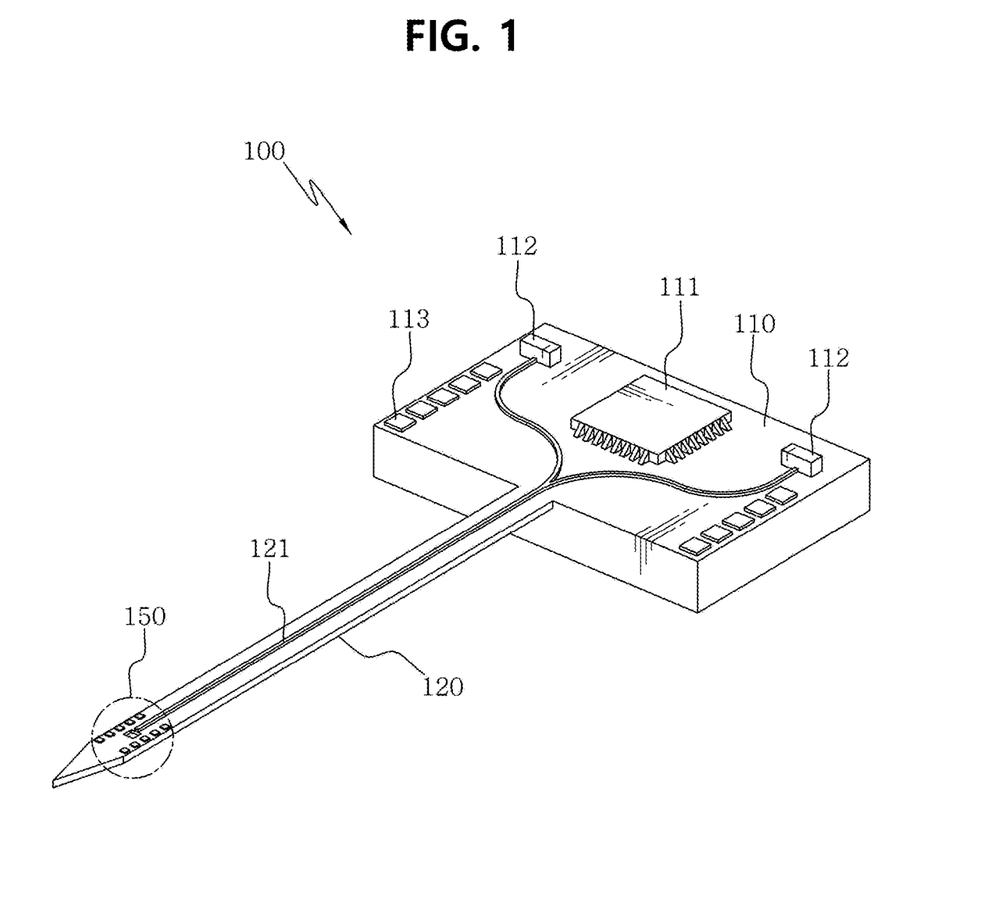
FIG. 1 is a perspective view of a neural probe structure according to an embodiment of the present disclosure.

FIG. 1 is a perspective view of a neural probe structure 100 according to an embodiment of the present disclosure. Referring to FIG. 1, the neural probe structure 100 includes a probe 120 that is inserted into a subject (not shown) and a body 110 to support and fix the rear end of the probe 120.

The size of the probe 120 may variously change according to usage environments (for example, the type of experiment, diagnosis, the state of treatment, etc.), and the probe 120 may be manufactured in a very small size of between a few pm and a few hundred of μm. For example, in an embodiment of the present disclosure, the neural probe structure 100 including the probe 120 of about 100-200 μm in width and about 20-40 μm in depth and a manufacturing method thereof will be described below by way of illustration.

As shown in FIG. 1, the body 110 includes an integrated circuit (IC) 111 and a light source 112. Additionally, the body 110 includes an optical waveguide 121 that extends along the probe 120 from the light source 112.

The neural probe structure 100 may include the IC 111 integrated in the body 110 for amplification of neural signals, analog-digital conversion and control of the light source 112 and wireless communication.

The IC 111 records signals from electrodes 122 and a photo diode 210, and controls the light source 112. That is, for the probe 120 inserted into the subject (not shown) to optically measure neural activity evoked using light transmitted through the optical waveguide 121 as described below, the IC 111 may record a fluorescence signal applied to the photo diode 210. Additionally, the IC 111 may adjust the interval and type of light transmitted through the optical waveguide 121 by controlling the light source 112.

The light source 112 may include at least one of a light emitting diode (LED), a laser and a lamp. The light source 112 may be configured to provide one or more wavelength ranges of light. For example, as shown in FIG. 1, different excitation wavelengths of light may be provided from a plurality of light sources 112 through the optical waveguide 121. Although FIG. 1 shows the body 110 including two LED light sources (e.g., red LED, green LED), this is just an embodiment and is not limited thereto, and various modifications may be made thereto.

A plurality of pads 113 may be arranged on top of the body 110. Each pad 113 may be electrically connected to each electrode 122 through a signal line (not shown) installed in the body 110 and the probe 120. Each pad 113 may be electrically connected to transmit neural response signals collected from the electrodes 122 to an external signal processing and analysis device (not shown).

The optical waveguide 121 extends from the light source 112 to the proximity of the photo diode 210. As shown in FIG. 1, when the plurality of light sources 112 is provided, the optical waveguide 121 may be connected to each light source 112 to form a plurality of input terminals. That is, a plurality of input waveguides may be combined into one waveguide (an optical mixer) to allow multiple fluorescence emission.

The light for neural stimulation transmitted from the light source 112 is guided through the optical waveguide 121. In this instance, for example, a cladding made of a material having a different refractive index from the optical waveguide 121 may be disposed on bottom of the optical waveguide 121. The optical waveguide 121 may be designed such that light guided through the optical waveguide 121 does not leak through the sides of the optical waveguide 121 by the cladding or air surrounding the sides of the optical waveguide 121 to cause the total internal reflection to occur. The light guided through the inside of the optical waveguide 121 by the total internal reflection may be outputted through the end of the optical waveguide 121 to apply optical neural stimulation.

Figure 2:
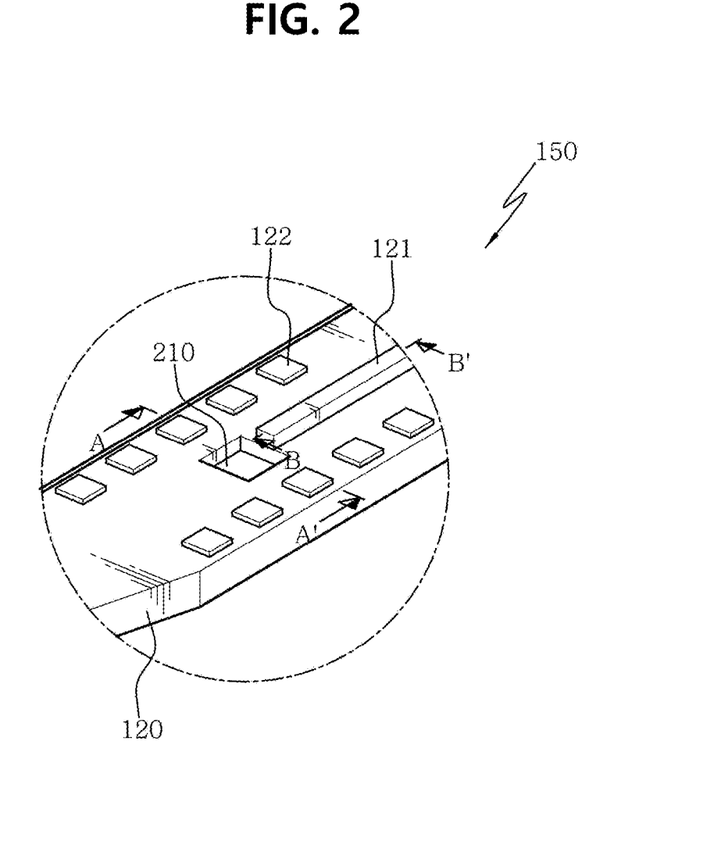
FIG. 2 is an enlarged view of a fluorescence measuring unit of a neural probe structure according to an embodiment of the present disclosure.

FIG. 2 is an enlarged view of a measuring unit 150 of the neural probe structure 100 according to an embodiment of the present disclosure.

Referring to FIG. 2, the neural probe structure 100 includes the measuring unit 150 at the end of the probe 120 to record an electrical/optical neural signal. The measuring unit 150 includes the end of the optical waveguide 121, the electrodes 122 and the photo diode 210.

The optical waveguide 121 may include a plurality of input waveguides to receive light from the plurality of light sources 112 disposed in the body 110, and a single output waveguide connected from the input waveguides and extending on the probe 120.

The single output terminal of the optical waveguide 121 extends to the proximity of the photo diode 210 as shown in FIG. 2. According to an embodiment of the present disclosure, the output terminal of the optical waveguide 121 may be connected up to the front of the photo diode 210, and the optical waveguide 121 may be formed at a larger height than the photo diode 210.

The electrodes 122 measure an electrical neural signal. The probe 120 may be so very small in size to be inserted into a local part of the subject's brain, and the electrodes 122 may be microelectrodes. According to an embodiment of the present disclosure, the electrodes 122 may be a microelectrode array including a plurality of microelectrodes, and can transmit an electrical neural signal to the IC 111 or the external signal processing and analysis device.

According to an embodiment of the present disclosure, the electrodes 122 may be made of metal and polymer that is conductive and highly biocompatible. The electrodes 122 may be formed near the photo diode 210 to optically record neural activity, and at the same time, measure an electrical neural signal.

The photo diode 210 optically measures neural activity evoked using light transmitted through the optical waveguide 121. That is, the photo diode 210 may measure a light emission signal from a cell labeled with a fluorescence specimen emitted through a specific wavelength of light transmitted through the optical waveguide 121, and convert it to an electrical signal.

The photo diode 210 may be integrally formed in a silicon (Si) substrate. For example, the photo diode 210 may be integrally formed in the silicon substrate probe based on a complementary metal-oxide semiconductor (CMOS) process as described below.

As shown in FIG. 2, the photo diode 210 may be made at a smaller height than the optical waveguide 121 to prevent light from being directly transmitted to the photo diode 210. When the photo diode 210 is made at a smaller height than the optical waveguide 121 to avoid light directly transmitted from the optical waveguide 121, it is possible to measure fluorescence emitted from neurons without a filter.

According to an embodiment of the present disclosure, the photo diode 210 may further include an optical filter. The photo diode 210 may include the optical filter formed by patterning, and in this case, it is possible to selectively measure fluorescence signals at a specific wavelength range, and increase the efficiency of selective measurement of fluorescence signals at a specific wavelength range.

Figure 3A:
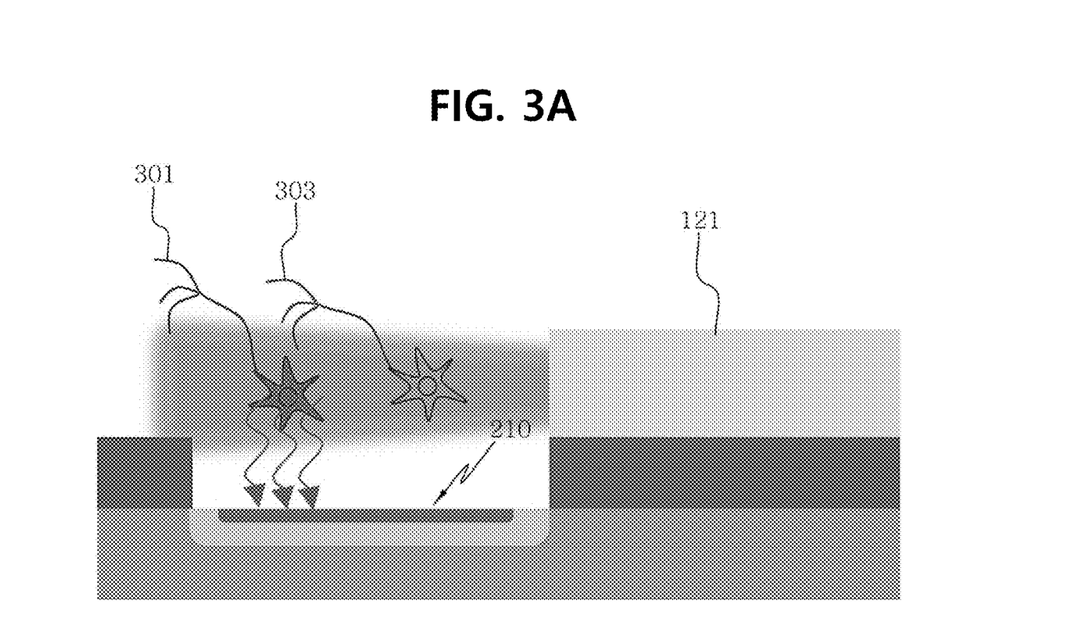
FIGS. 3A and 3B schematically show the multiple fluorescence signal measurement principle of a neural probe structure according to an embodiment of the present disclosure.
Figure 3B:
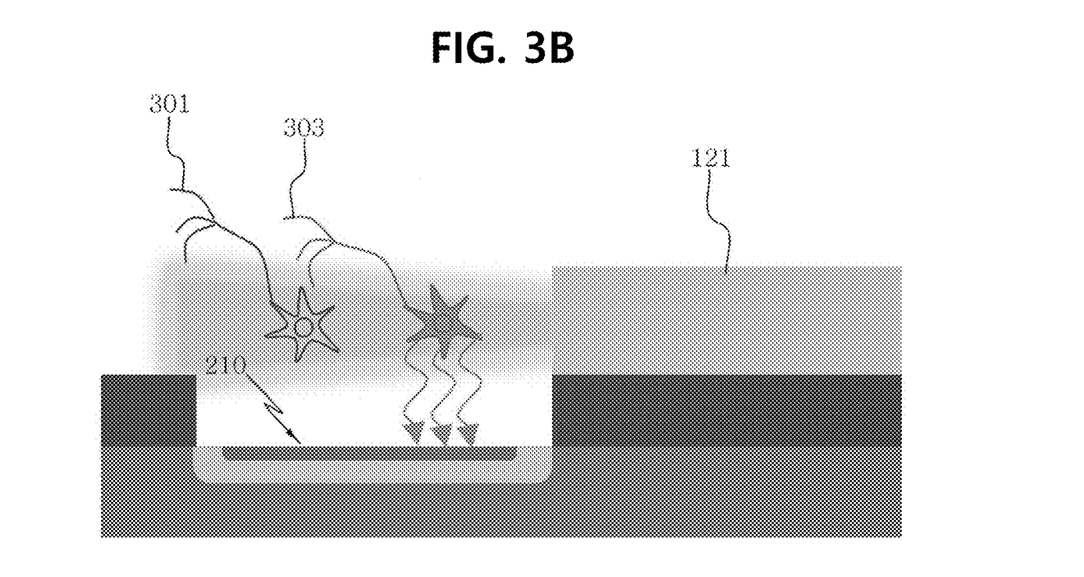

FIGS. 3A and 3B schematically show the multiple fluorescence signal measurement principle of the neural probe structure 100 according to an embodiment of the present disclosure.

Referring to FIGS. 3A and 3B, according to an embodiment of the present disclosure, shown is an example of optical measurement of neural activity evoked using light from blue and yellow LED light sources in the subject with calcium indicator labeled neurons.

A target cell in the subject is labeled with a fluorescence specimen by infecting the target cell with virus. Referring to FIGS. 3A and 3B, shown are a neuron 301 labeled with green fluorescent protein based calcium indicator GCaMP and a neuron 303 labeled with red fluorescent protein based calcium indicator RCaMP.

As shown in FIG. 3A, when an excitation wavelength of light is transmitted through the optical waveguide 121 with the probe 120 of the neural probe structure 100 being inserted near the neuron 301 labeled with GCaMP and the neuron 303 with RCaMP, only the neuron 301 labeled with GCaMP emits a green fluorescence signal.

Additionally, as shown in FIG. 3B, when a different excitation wavelength of light is transmitted through the optical waveguide 121 with the probe 120 of the neural probe structure 100 being inserted near the neuron 301 labeled with GCaMP and the neuron 303 labeled with RCaMP, only the neuron 303 labeled with RCaMP emits a red fluorescence signal.

As shown in FIGS. 3A and 3B, the photo diode 210 may be disposed at lower position than the optical waveguide 121 to prevent the excitation wavelength of light from being directly transmitted to the photo diode 210. Since the fluorescence emission signal from the cell, to which the excitation wavelength of light is transmitted, travel uniformly in all directions, the photo diode 210 may receive the fluorescence emission signal while avoiding the excitation wavelength of light directly transmitted, thereby recording the fluorescence signal without a filter.

According to an embodiment of the present disclosure, the neural probe structure 100 may include a plurality of light sources 112 to transmit different excitation wavelengths of light to express two or more types of calcium indicators. That is, two or more excitation wavelengths of light may be inputted at a time interval to record multiple types of fluorescence signals. The photo diode 210 may convert the fluorescence signals to electrical signals and transmit them to the IC 111 or the external signal processing and analysis device, thereby recording the signals from activated cells in the human body, and at the same time, classifying the type of the cells.

FIGS. 4A to 4K exemplarily show a detailed process of manufacturing the neural probe structure 100 according to an embodiment of the present disclosure. According to an embodiment of the present disclosure, the photo diode 210 may be formed in a silicon substrate based on a CMOS process. Additionally, according to an embodiment of the present disclosure, since the probe 120 is about 100-200 μm in width and about 20-40 μm in depth, the photo diode 210 and the electrodes 122 provided in the probe 120 may be formed to conform to the size of the probe 120.

For convenience of description, hereinafter, FIGS. 4A to 4K show a combination of horizontal cross section of the probe 120 of FIG. 2 taken along AA' and vertical cross section view taken along BB'.

Figure 4A:
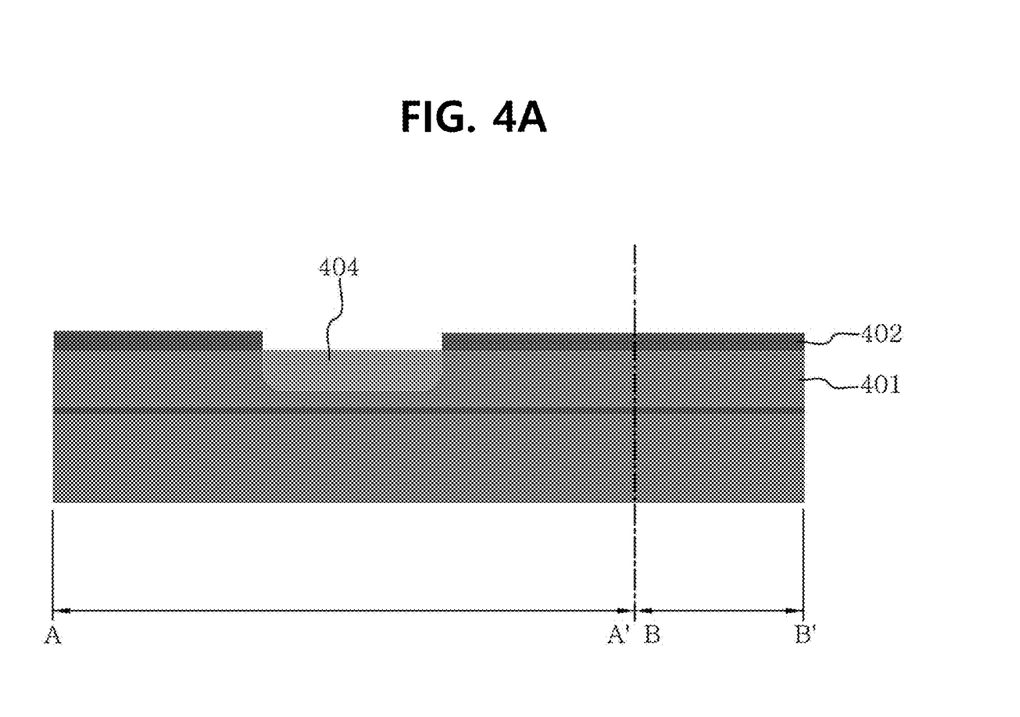
FIGS. 4A to 4K show a process of manufacturing a neural probe structure according to an embodiment of the present disclosure.

As shown in FIG. 4A, first, a silicon-on-insulator (SOI) substrate 401 is prepared, and a grown (e.g., thermally grown) $SiO_2$ layer 402 is formed. Subsequently, an N-type substrate layer 404 is formed by forming an n-well pattern on the substrate 401 through a photolithography oxide patterning process using a mask and performing ion implantation.

Figure 4B:
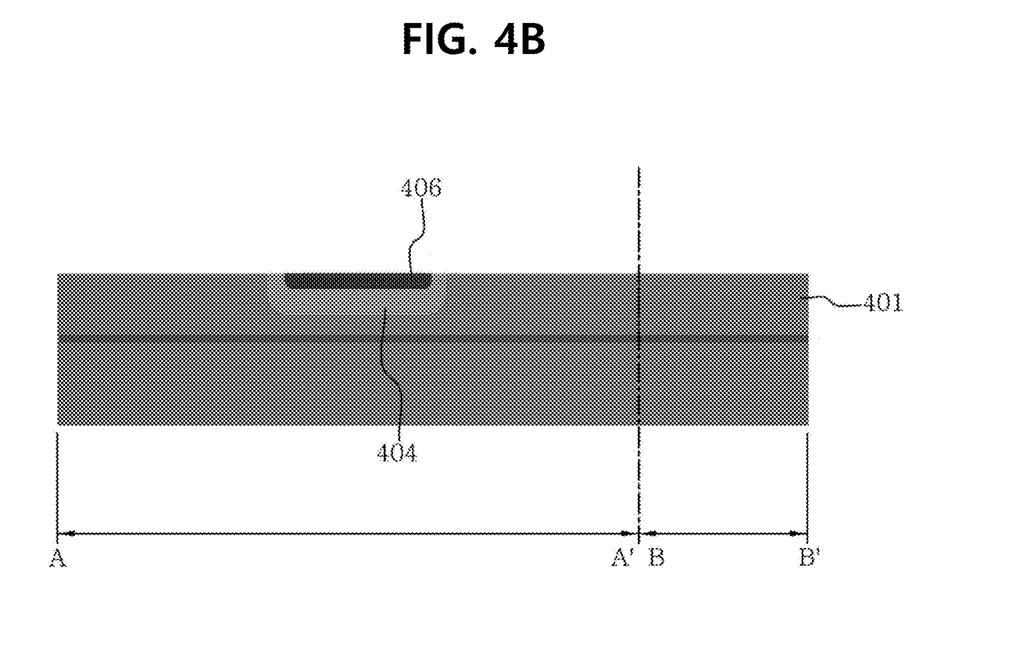

Subsequently, as shown in FIG. 4B, an n+ layer 406 is formed by forming an n+ layer pattern through photolithography using a mask and performing n+ implantation.

Figure 4C:
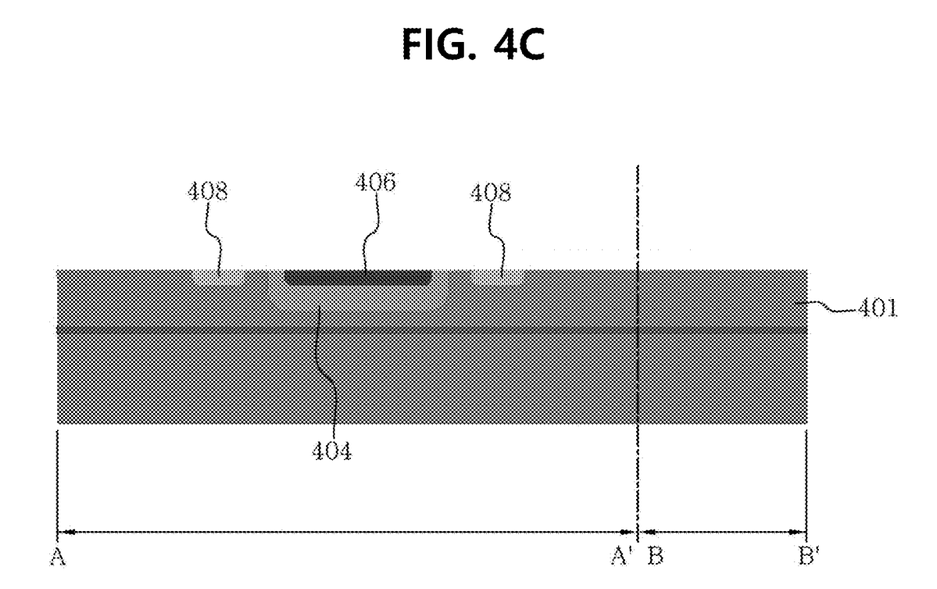

Subsequently, as shown in FIG. 4C, a p+ layer 408 is formed by forming a p+ layer pattern through photolithography using a mask and performing p+ implantation.

Figure 4D:
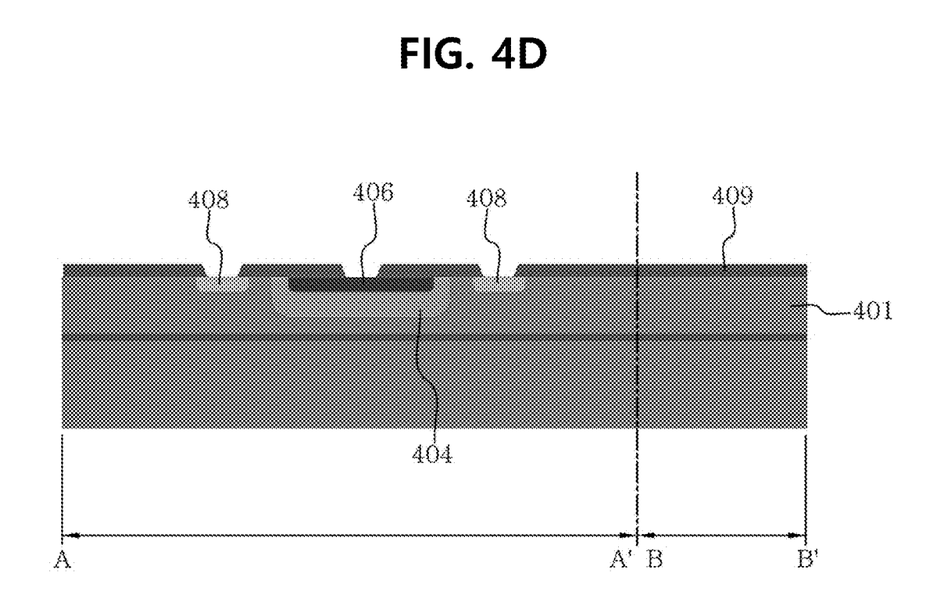

Subsequently, as shown in FIG. 4D, a $SiO_2$ layer 409 is deposited. In this instance, for example, the $SiO_2$ layer 409 may be deposited by plasma enhanced chemical vapor deposition (PECVD). Subsequently, a pattern is formed in the $SiO_2$ layer 409 on the n+ layer 406 and the p+ layer 408 through photolithography using an etching mask and wet etching.

Figure 4E:
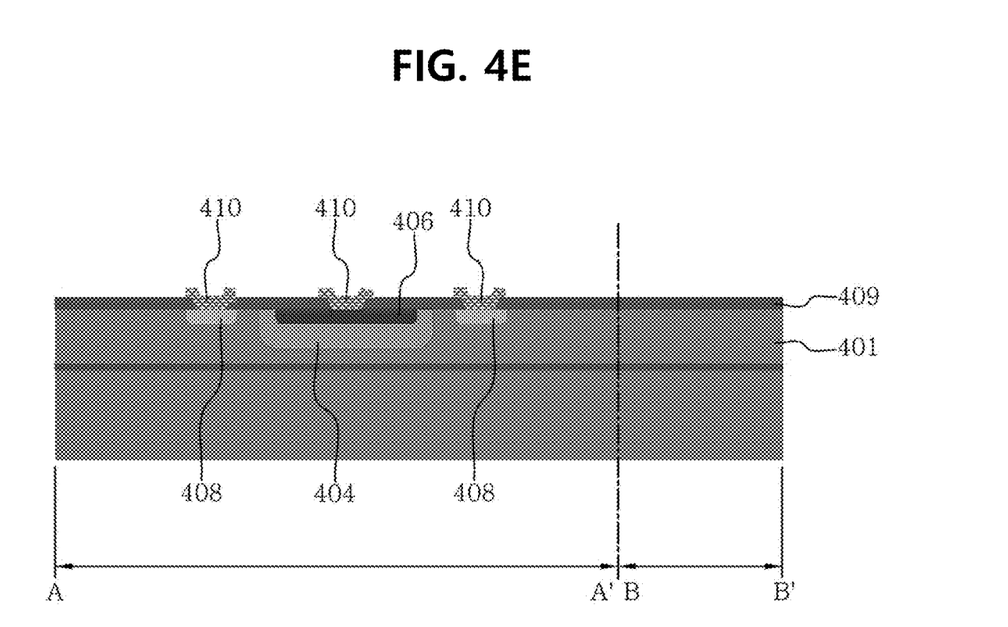

Subsequently, as shown in FIG. 4E, a metal layer 410 is formed in contact with the n+ layer 406 and the p+ layer 408.

The metal layer 410 is formed by defining an etching pattern in the metal layer 410 on the n+ layer 406 and the p+ layer 408 through photolithography and patterning through wet etching.

Through the process of FIGS. 4A to 4E, the substrate having the photo diode 210 of the neural probe structure 100 of FIG. 1 may be prepared.

Figure 4F:
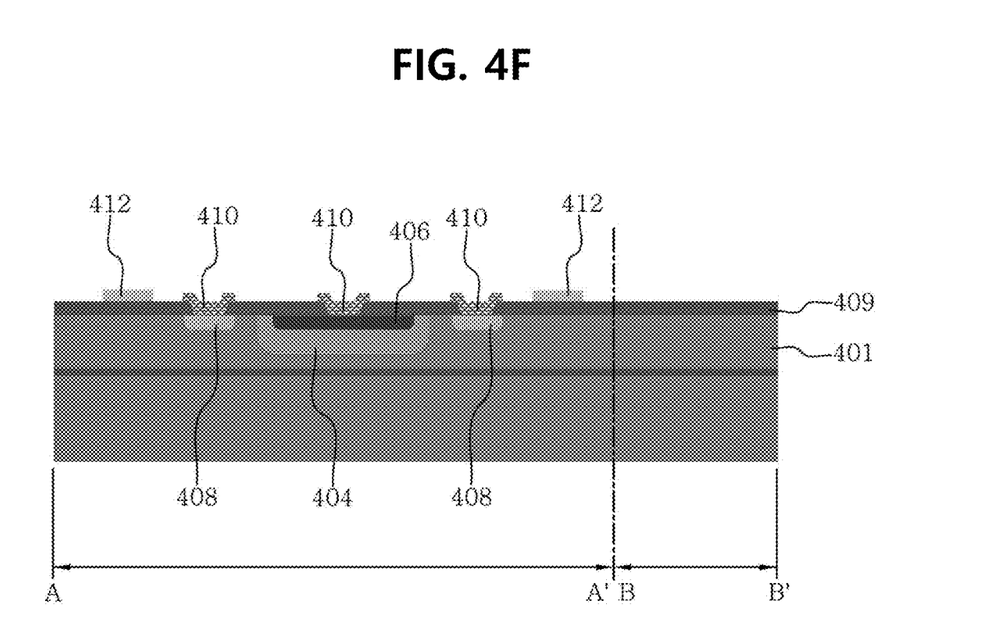

As shown in FIG. 4F, subsequently, an electrode layer is formed on top. The electrode layer 412 is formed by defining an etching pattern in the electrode layer through photolithography and patterning through etching. In this instance, for example, the patterning of the electrode layer 412 may be performed using an inductively coupled plasma reactive ion etching (ICP RIE) system. The generated electrode layer 412 may be the electrodes 122 of the neural probe structure 100 for measuring an electrical neural signal.

Figure 4G:
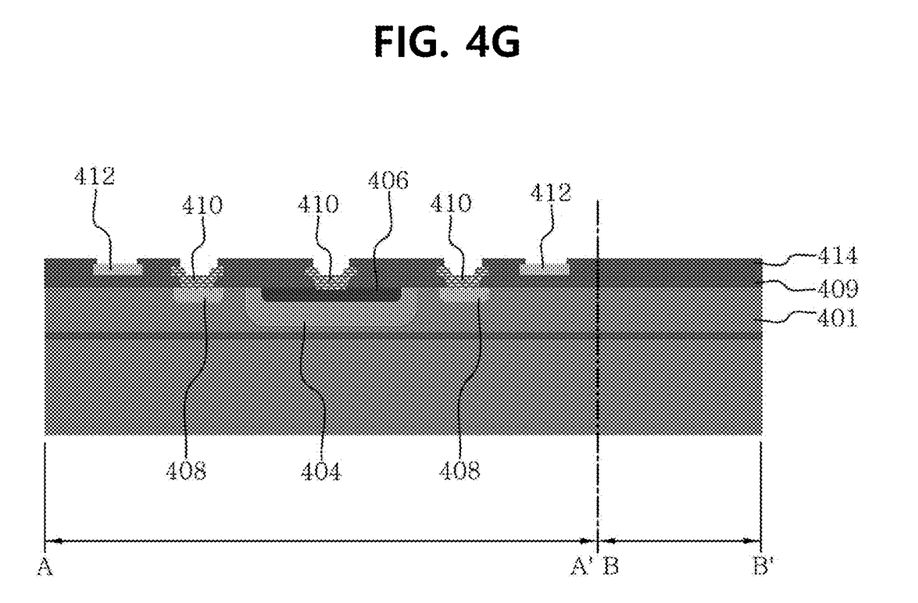

Subsequently, as shown in FIG. 4G, for example, a $SiO_2$ layer 414 is deposited on top by PECVD. Additionally, a pattern is formed in the $SiO_2$ layer 414 through photolithography oxide patterning using a mask and etching. In this instance, according to an embodiment of the present disclosure, the $SiO_2$ layer 414 may be formed by patterning through dry etching.

Figure 4H:
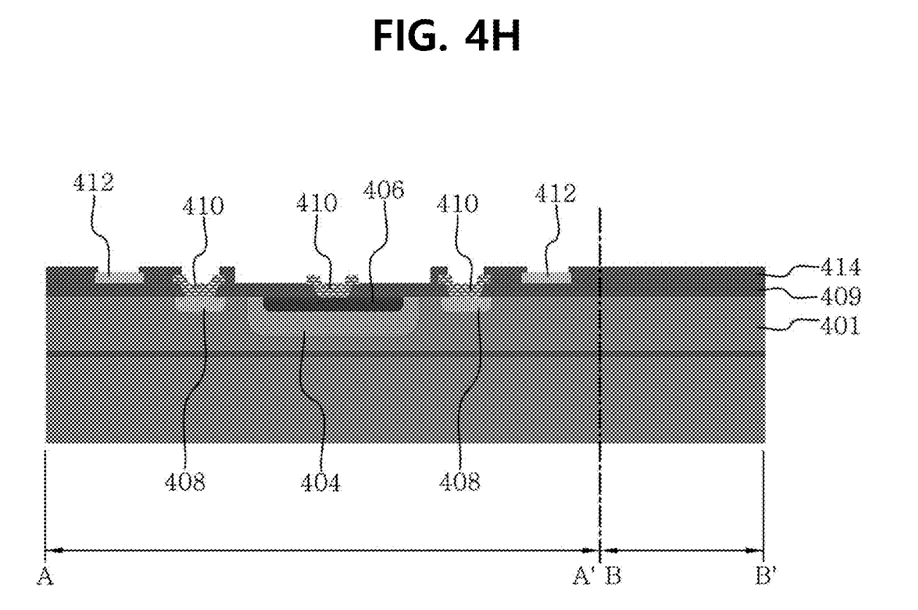

Subsequently, as shown in FIG. 4H, a pattern is formed in the $SiO_2$ layer 414 through photolithography using an etching mask and etching again.

Through the process up to FIG. 4H, the substrate having the photo diode 210 and the electrodes 122 of the neural probe structure 100 of FIG. 1 may be prepared. Through this process, the photo diode 210 may be completely embedded in the probe 120 so that the photo diode 210 does not protrude above the top of the probe 120.

Figure 4I:
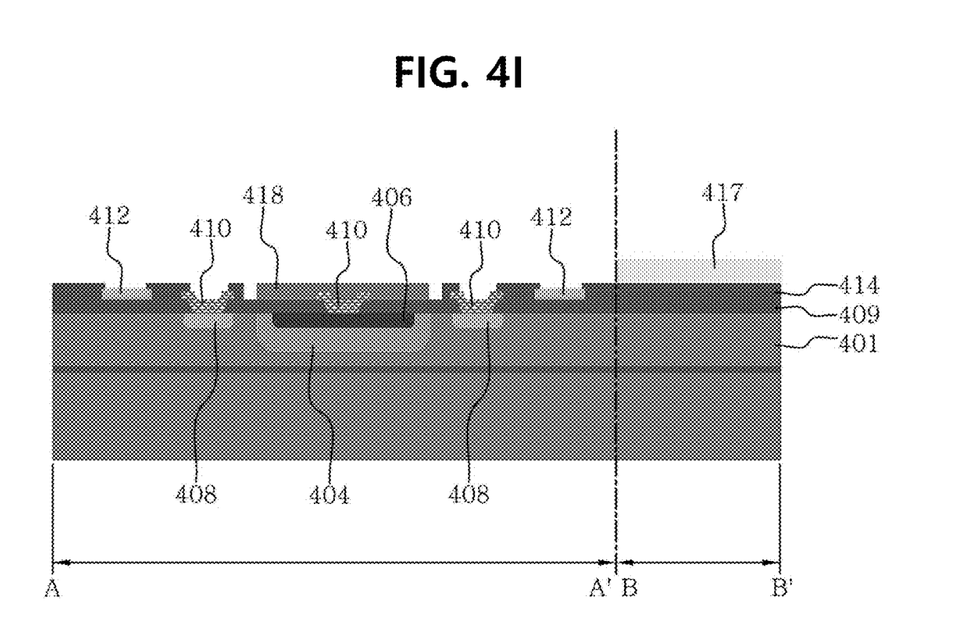

Subsequently, as shown in FIG. 4I, an optical filter layer 418 is formed on the $SiO_2$ layer 409 (the photo diode 210) and an optical waveguide layer 417 is formed on the $SiO_2$ layer 414 each through photolithography. According to other embodiments of the present disclosure, the optical filter layer 418 may be omitted.

Figure 4J:
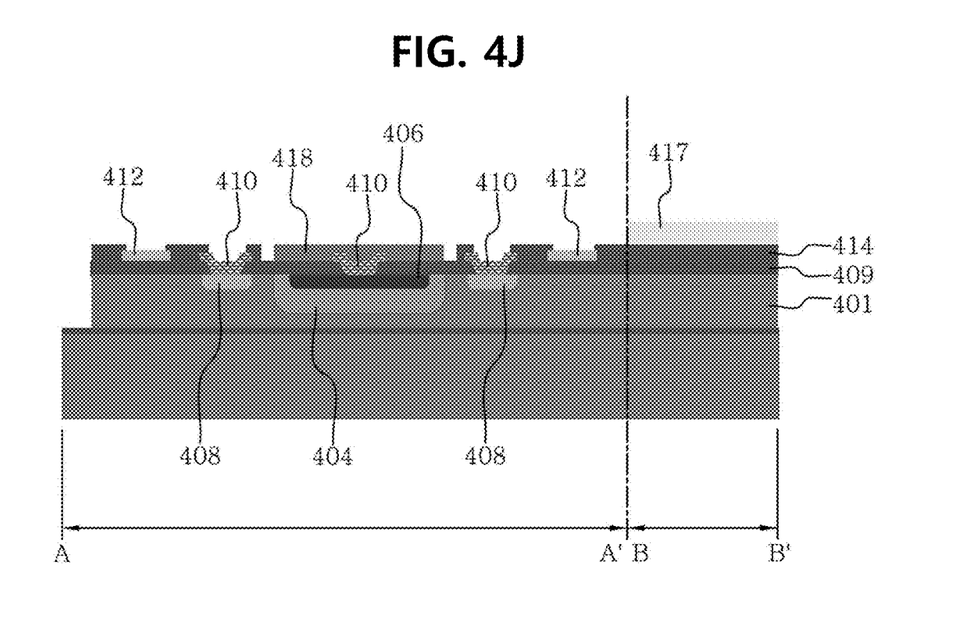

Subsequently, as shown in FIG. 4J, photolithography using a mask and deep reactive-ion etching (DRIE) (front side DRIE) may be performed for patterning by etching an insulating film ($SiO_2$) of the SOI substrate 401.

Figure 4K:
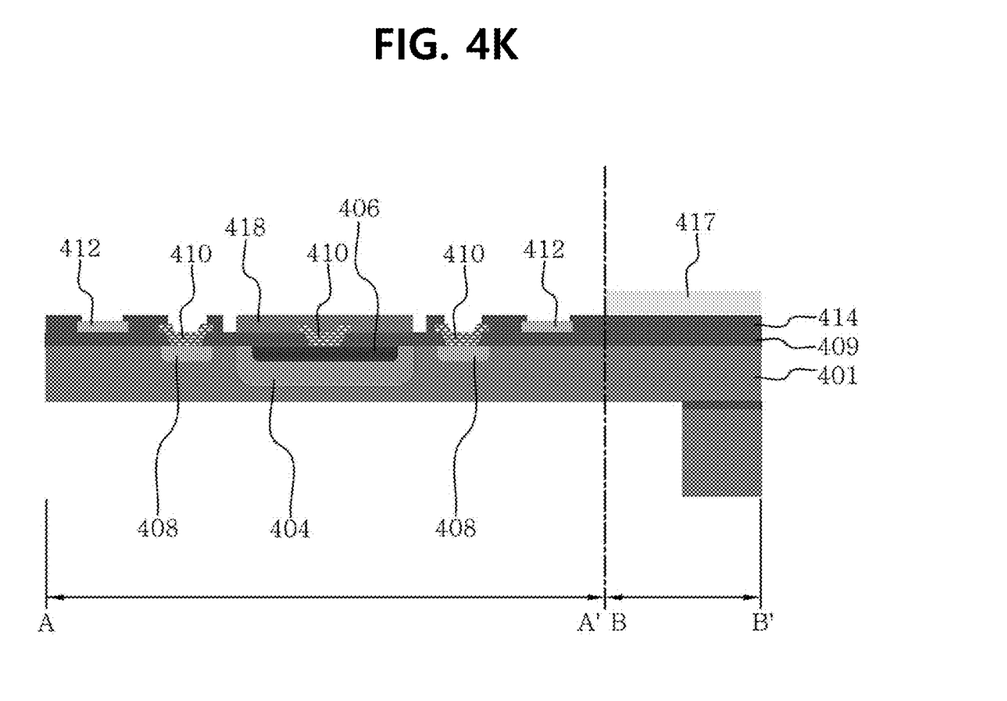

Finally, as shown in FIG. 4K, a carrier wafer is attached to the upper surface, and photolithography using a DRIE mask and DRIE (back side DRIE) is performed on the lower surface of the substrate. The carrier wafer is removed, followed by cleaning and separation from the system, and finally, the substrate etched as shown in FIG. 4K is prepared.

Through the process up to FIG. 4K, the neural probe structure 100 of FIG. 1 including the photo diode 210, the electrodes 122 and the optical waveguide 121 (and optionally including the optical filter) may be manufactured.

The photo diode 210 according to an embodiment of the present disclosure is formed at a smaller height than the optical waveguide 121 to prevent the excitation wavelength of light transmitted from the optical waveguide 121 from being directly transmitted to the photo diode 210. In this embodiment, the photo diode 210 is formed at a smaller height than the optical waveguide 121 by the thickness of the $SiO_2$ layer 414.

According to this configuration, the photo diode 210 receives a fluorescence emission light from a cell to which the excitation wavelength of light is transmitted, while avoiding the excitation wavelength of light directly transmitted from the optical waveguide 121, thereby recording a fluorescence signal without an optical filter. By this reason, it is possible to record multiple types of fluorescence signals upon receiving two or more different wavelengths of light.

According to another embodiment of the present disclosure, the photo diode 210 may have an additionally patterned optical filter to increase the efficiency of selective measurement of fluorescence signals at a specific wavelength.

Additionally, as described above, since the optical waveguide 121, the photo diode 210 and the microelectrode array including the electrodes 122 is integrated in the probe 120, it is possible to optically measure neural activity evoked using a specific wavelength of light in the subject in which the probe 120 is mounted, using the optical waveguide 121 and the photo diode 210, and at the same time, record an electrical neural signal using the microelectrode array.

The neural probe structure according to various embodiments of the present disclosure is manufactured in a small size for use in a wide range of neural circuit research applications. Additionally, with a structure in which the optical waveguide, the photo diode and the microelectrode array are integrated in the probe, it is possible to optically measure neural activity evoked using a specific wavelength of light, and at the same time, record an electrical neural signal.

In addition, the proposed neural probe structure includes the photo diode formed at a smaller height than the optical waveguide to prevent light transmitted from the optical waveguide from being directly transmitted to the photo diode, thereby measuring fluorescence signals emitted from cells without a filter. Additionally, as the optical waveguide is configured to receive different wavelengths of light from a plurality of light sources, it is possible to measure multiple fluorescence signals. Through this, it is possible to observe multiple types of fluorescence signals at a local area of the neural probe, thereby recording neural activity and classifying the type of cells. The proposed neural probe structure may be used in a wide range of applications including not only a variety of nerve research but also treatment and diagnosis of diseases.

The effect that can be obtained from the present disclosure is not limited to the above-mentioned effects, and other effects not mentioned herein will be clearly understood by those having ordinary skill in the art from the foregoing description.

What is claimed is:

1. A neural probe structure, comprising:
    a probe configured to be inserted into a subject;
    a body which supports a rear end of the probe;
    at least one light source included in the body;
    a photo diode formed in the probe;
    a plurality of electrodes formed in the probe; and
    an optical waveguide extending from the at least one light source in the body to the photo diode of the probe,
    wherein the photo diode includes p+ layer and n+ layer, and
    an insulating layer is further disposed under the plurality of electrodes and above the p+ layer and n+ layer of the photo diode.

2. The neural probe structure according to claim 1, further comprising:
    an optical filter on the photo diode.

3. The neural probe structure according to claim 1, wherein when the body includes a plurality of light sources, the optical waveguide is formed such that a plurality of branches each extends from the plurality of light sources, the branches are combined into one strand at a point, and the strand extends to the photo diode.

4. The neural probe structure according to claim 1, wherein the photo diode is formed in a concave shape inwards from an upper surface of the probe to prevent the photo diode from protruding above the upper surface of the probe.

5. The neural probe structure according to claim 1, wherein the photo diode measures a fluorescence signal emitted from a neuron by light transmitted from the at least one light source through the optical waveguide, and
the plurality of electrodes is arranged near the photo diode to measure an electrical neural signal of the neuron.

6. A method for manufacturing a neural probe structure defined in claim 1, the method comprising:
forming the photo diode in a substrate that constitutes the probe; and
forming the optical waveguide at a larger height than the photo diode along a longitudinal axis from the photo diode.

7. The method for manufacturing a neural probe structure according to claim 6, further comprising:
forming an optical filter on the photo diode.

8. The method for manufacturing a neural probe structure according to claim 6, wherein forming the optical waveguide comprises, when the body includes a plurality of light sources, forming the optical waveguide such that a plurality of branches each extends from the plurality of light sources, the branches are combined into one strand at a point, and the strand extends to the photo diode.

9. The method for manufacturing a neural probe structure according to claim 6, wherein forming the photo diode in the substrate comprises forming the photo diode in a silicon substrate based on a complementary metal-oxide semiconductor (CMOS) process.

10. The method for manufacturing a neural probe structure according to claim 6, wherein forming the photo diode in the substrate comprises forming the photo diode in the substrate into a concave shape inwards from an upper surface of the probe to prevent the photo diode from protruding above the upper surface of the probe.

11. The method for manufacturing a neural probe structure according to claim 6, further comprising:
forming a plurality of electrodes at locations a predetermined distance away from two sides along a latitudinal axis from the photo diode.

* * * * *